(12) United States Patent
Steckmann et al.

(10) Patent No.: US 10,215,678 B2
(45) Date of Patent: Feb. 26, 2019

(54) SYSTEMS AND METHODS FOR MAXIMUM SPECIFIC GRAVITY TESTS FOR ASPHALT MIXTURE SAMPLES

(71) Applicant: InstroTek, Inc., Raleigh, NC (US)

(72) Inventors: Dirk M. Steckmann, Raleigh, NC (US); Ali Regimand, Raleigh, NC (US); Lawrence H. James, Raleigh, NC (US); Andrew T. LaCroix, Raleigh, NC (US); Johnny G. Williams, Jr., Raleigh, NC (US); Adam C. O'Neill, Durham, NC (US)

(73) Assignee: InstroTek, Inc., Raleigh, NC (US)

( * ) Notice: Subject to any disclaimer, the term of this patent is extended or adjusted under 35 U.S.C. 154(b) by 233 days.

(21) Appl. No.: 15/225,322

(22) Filed: Aug. 1, 2016

(65) Prior Publication Data
US 2018/0031461 A1   Feb. 1, 2018

(51) Int. Cl.
  *G01N 9/36* (2006.01)
  *G01N 9/26* (2006.01)
  *G01N 33/42* (2006.01)

(52) U.S. Cl.
  CPC ............. *G01N 9/36* (2013.01); *G01N 9/26* (2013.01); *G01N 33/42* (2013.01)

(58) Field of Classification Search
  CPC ............. G01N 9/36; G01N 9/26; G01N 33/42
  See application file for complete search history.

(56) References Cited

U.S. PATENT DOCUMENTS

| | | | | |
|---|---|---|---|---|
| 3,944,188 A | * | 3/1976 | Parker | B01F 11/0014 366/110 |
| 5,365,793 A | * | 11/1994 | Terrel | G01N 3/36 73/38 |
| 6,799,471 B1 | * | 10/2004 | Regimand | G01N 3/36 137/386 |
| 8,408,013 B2 | * | 4/2013 | Muse | B01D 53/265 62/3.4 |
| 2001/0002412 A1 | * | 5/2001 | Kolarik | B28B 11/04 523/210 |

* cited by examiner

*Primary Examiner* — Francis C Gray
(74) *Attorney, Agent, or Firm* — Myers Bigel, P.A.

(57) ABSTRACT

A system for conducting a maximum specific gravity test includes a sealable container for receiving and holding an asphalt mixture sample, a vacuum pump in fluid communication with the container for evacuating the container, a valve in fluid communication with the container, a shaker for shaking the container, and a controller. The controller can operate the system in a test mode by: (i) turning on the vacuum pump; (ii) automatically monitoring a vacuum pressure in the container with the vacuum pump on; (iii) automatically turning on the shaker when the monitored vacuum pressure reaches a target vacuum pressure value; (iv) automatically opening or closing the valve such that the monitored vacuum pressure in the container is maintained within a target vacuum pressure range for a predetermined period of time with the shaker on; and (v) automatically turning the shaker off at the end of the predetermined period of time.

20 Claims, 4 Drawing Sheets

SYSTEMS AND METHODS FOR MAXIMUM SPECIFIC GRAVITY TESTS FOR ASPHALT MIXTURE SAMPLES

BACKGROUND

One of the most important tests in the construction industry is the Theoretical Maximum Specific Gravity Test, often called the "Rice test." In this test a sample of loose asphalt mixture is placed in a calibrated container. Water is added to the container to cover the sample. The container is sealed and exposed to 27.5±2.5 mmHg of vacuum pressure. The sealed container is placed on a shaker and shaken under the 27.5±2.5 mmHg of vacuum pressure for 15 minutes. Shaking along with vacuum helps ensure that air and trapped air bubbles are removed from the sealed container. After 15 minutes of shaking, the container is allowed to come back to atmospheric pressure. The calibrated container is then submerged in a water tank equipped with a scale and a submerged or underwater weight of the container and sample is determined. Knowing the initial dry weight (mass) of the sample (A), underwater mass of the container (B) and submerged total weight of the container and sample (C), maximum specific gravity of the asphalt mixture can be determined using the below equation.

$$\text{Theoretical Maximum Specific Gravity} = Gmm = \frac{A}{A-(C-B)}.$$

This test procedure is covered under American Society of Testing and Materials (ASTM) D2041 standard and American Association of State Highway and Transportation Officials (AASHTO) T209 standard. These test standards provide alternative ways of measuring the weights of samples after vacuum operation and suitable containers for the test. The results from the test are used throughout the mixture design process for asphalt pavements and for determination of total air void content in compacted asphalt in the laboratory and the field. In almost all pavement jobs, percent air void is a quality control measure for compaction and can be used for acceptance and rejection of a pavement job or batch.

Limitations related to this test are manual adjustment of the vacuum level, the precise time when the shaker is turned on when vacuum approaches the nominal value, the precise amount of time the shaker is left on, and the frequency and quality of shaking instruments used. All these factors can affect the accuracy of the test and repeatability of results, particularly between different users and/or testing facilities.

SUMMARY

Some embodiments of the invention are directed to a system for conducting a maximum specific gravity test. The system includes a sealable container sized and configured to receive and hold an asphalt mixture sample, a vacuum pump in fluid communication with the container and configured to evacuate the container, a valve in fluid communication with the container and configured to adjust vacuum pressure in the container, a shaker configured to shake the container, and a controller. The controller is configured to operate the system in a test mode by: (i) turning on the vacuum pump; then (ii) automatically monitoring a vacuum pressure in the container with the vacuum pump on; then (iii) automatically turning on the shaker when the monitored vacuum pressure reaches a target vacuum pressure value; then (iv) automatically opening or closing the valve such that the monitored vacuum pressure in the container is maintained within a target vacuum pressure range for a predetermined period of time with the shaker on; and then (v) automatically turning the shaker off at the end of the predetermined period of time.

Some other embodiments of the invention are directed to a method for conducting a maximum specific gravity test. The method includes: placing an asphalt mixture sample in an interior of a container that is held on a shaker; adding water to the interior of the container to submerge the asphalt mixture sample; sealing the interior of the container using a lid; automatically turning on a vacuum pump that is in fluid communication with the interior of the container to evacuate the interior of the container; automatically monitoring a vacuum pressure in the interior of the container using a controller; automatically turning on the shaker when the monitored vacuum pressure is about 27.5 mmHg using the controller; using the controller, automatically opening a valve that is between the container and the vacuum pump if the monitored vacuum pressure falls below 27.5 mmHg by a first prescribed amount; using the controller, automatically closing the valve if the monitored vacuum pressure exceeds 27.5 mmHg by a second prescribed amount; and automatically turning off the shaker about 15 minutes after automatically turning on the shaker.

Some other embodiments of the invention are directed to a control unit for automating a maximum specific gravity test. The control unit includes a housing, a vacuum pump outlet on the housing for electrically connecting a vacuum pump to the control unit, a shaker outlet on the housing for electrically connecting a shaker to the control unit, an inlet port on the housing for fluidly connecting a container to the control unit, with the container being on the shaker and in fluid communication with the vacuum pump, and a valve in the housing and in fluid communication with the inlet port. The control unit is configured to turn on the vacuum pump, to automatically monitor a vacuum pressure in the container with the vacuum pump on, to automatically turn on the shaker when the monitored vacuum pressure reaches about 27.5 mmHg, to automatically open or close the valve when the monitored vacuum pressure falls outside the range of 27.5 mmHg±2.5 mmHg, and to automatically turn off the shaker 15 minutes after automatically turning on the shaker.

Further features, advantages and details of the invention will be appreciated by those of ordinary skill in the art from a reading of the figures and the detailed description of the preferred embodiments that follow, such description being merely illustrative of the invention.

DETAILED DESCRIPTION

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises," "includes," "comprising," and/or "including," when used in this specification, specify the presence of stated features, integers, steps, operations, elements, and/or components, but do not preclude the presence or addition of one or more other features, integers, steps, operations, elements, components, and/or groups thereof.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "automatically" means that the operation is substantially, and may be entirely, carried out without human or manual control, direction and/or input, and can be programmatically directed or carried out.

The term "programmatically" refers to operations directed and/or primarily carried out electronically by computer program modules, code and/or instructions.

Figure 1:
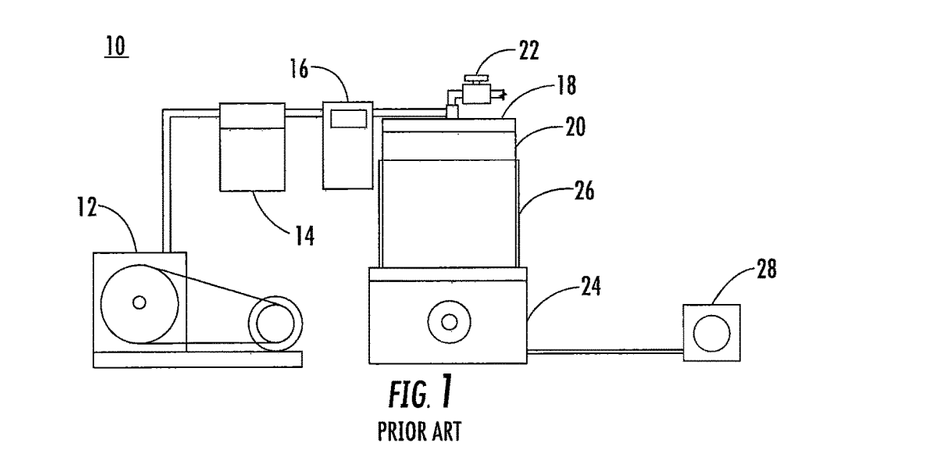
FIG. 1 is a schematic illustration of a conventional system for conducting a maximum specific gravity test.

FIG. 1 illustrates a conventional system 10 used to perform the Rice test to determine maximum specific gravity of an asphalt mixture sample. A vacuum pump 12 is connected pneumatically to an air dryer 14 and to a pressure gauge 16 which is connected to a sealable lid 18 of an aggregate binder mixture container 20. The sealable lid 18 is also connected to manual valve 22. The container 20 is clamped onto an electrically driven shaker 24 using a clamp 26. The electrically driven shaker 24 may be connected to a timer 28.

The asphalt mixture sample (e.g., aggregate binder mixture) is placed in the container 20 and completely covered with water. The container 20 is then placed on the electrically driven shaker 24 and clamped to the shaker 24 using the clamp 26. The sealable lid 18 is placed on the container 20 and the vacuum pump 12 turned on. The valve 22 is manually adjusted until the vacuum air pressure in the container 20 is 27.5±2.5 mmHg. When the correct air pressure is reached, the electrically driven shaker 24 is turned on and the timer 28 is set for 15 minutes. The air pressure is monitored using the air pressure gauge 16 and, if the air pressure falls outside the required limits, the valve 22 is manually adjusted until the air pressure is within the required range. When the timer 28 indicates that 15 minutes has elapsed, the electrically driven shaker 24 is turned off and the vacuum pump 12 is turned off. The valve 22 is then fully opened to allow the container 20 to return to atmospheric pressure.

There are various problems with this conventional system. First, the test standards require a precise vacuum in the sample container (the required pressure is generally a nominal 27.5±2.5 mmHg). In the conventional system, the vacuum is controlled manually by adjusting the air leakage rate into the system which is connected to the vacuum pump. When the pressure reaches 27.5 mmHg, the amount of air let into the system through the manually adjustable valve is equal to the air removed by the vacuum pump. This maintains the system at 27.5 mmHg. However, the technician must continuously monitor the vacuum pressure and readjust the air flow through the valve to maintain the proper pressure. This often leads to error in maintaining the proper pressure level for the required time.

Also, the conventional test system requires the shaker to be turned on when pressure in the container reaches 27.5±2.5 mmHg. The time to reach the required vacuum varies depending on the quality, age and size of the vacuum pump. Many technicians do not pay attention to this requirement and turn the shaker on when the pump is turned on or may not turn the shaker on precisely at the time the nominal pressure is manually achieved.

In addition, there are currently no requirements on the shaker used for this process. There are a number of different manufacturers that offer shaking instruments. If the shaking is too violent, the material in the container can compact, thereby trapping air in the sample and, for some materials, the bitumen film can strip away from the aggregates. If the shaking is too gentle, air and air bubbles may not be removed from the container. Improper shaking of the container during this test can result in inaccurate results and poor repeatability between facilities testing the same mixture.

Therefore, a system that automates, controls and monitors the testing process would improve the accuracy and repeatability of the test and would reduce operator involvement and the time the operator spends on the test. As described in more detail below, some embodiments of the invention provide a system that is capable of turning on the vacuum pump, automatically adjusting the vacuum pressure, automatically turning on the shaker and precisely timing the run times for the pump and the shaker. Some embodiments of the invention provide a system that monitors and reports the frequency and/or acceleration of the shaker induced vibration on the container. Some embodiments of the invention provide a system that is capable of storing and receiving data from other devices for reporting and automation purposes.

Figure 2:
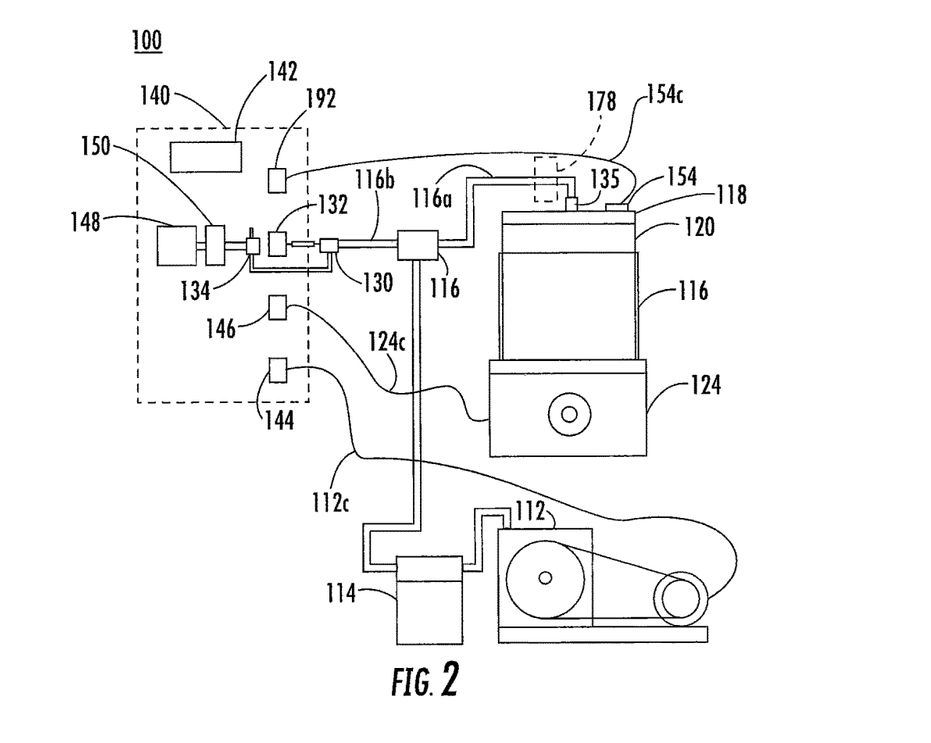
FIG. 2 is a schematic illustration of a system for conducting a maximum specific gravity test according to some embodiments of the invention.

FIG. 2 illustrates a system 100 used to perform the Rice test according to embodiments of the invention. A vacuum pump 112 is connected to a dryer 114 (e.g., a moisture trap or desiccant dryer) that is connected to (or in fluid communication with) a junction 116. Two air lines emerge from the junction 116: one 116a connecting to a sealable lid 118 for sealing a container 120 and one 116b to connect to a second junction 130 that is then connected to an air pressure sensor or vacuum gauge 132. A second line 131 emerges from the second junction 130 that connects to a valve 134 that is in fluid communication with an inlet port 135 of the lid 118 and/or the container and can vary the vacuum air pressure observed in the container 120. These lines may be or include hoses, pipes, tubes or the like. The junction 116 may be omitted as described in more detail below in reference to FIG. 4.

Automatic control of the maximum specific gravity test is achieved using a controller or control unit 140. The controller 140 may include at least one microprocessor. For example, a microprocessor 142 may be used to monitor the air pressure sensor 132. The microprocessor 142 may turn the vacuum pump 112 on and off optionally using microprocessor controlled relay 144. The microprocessor 142 may turn an electrically driven agitator or shaker 124 on and off optionally using microprocessor controlled relay 146.

According to some embodiments, vacuum air pressure control is achieved using a stepper motor 148 controlled by microprocessor 142 connected to an encoder 150 which drives (e.g., opens and closes) the valve 134. The air pressure sensor 132 is monitored by the microprocessor 142. If the air pressure is lower than the requested or target value, the valve 134 is opened by stepper motor 148 until the correct air pressure is achieved. If the air pressure is higher than the requested or target value, the valve 134 is turned by stepper motor 148 to close the valve 134 until the air pressure is at the correct value.

The acceleration or amplitude of the shaker 124 is monitored by an accelerometer 154. The signal from the accelerometer 154 may be monitored by the microprocessor 142 and is analyzed to determine the acceleration of the shaker 124. The accelerometer 154 may be connected to the controller 140 using a cable or cord 154c.

The container 120 (which may be a pycnometer) is placed on the shaker 124 and held thereon using a coupling feature (for example, the container 120 may be clamped to the shaker 124 using a clamp 116). An asphalt sample such as an aggregate binder mixture sample is placed in the container 120 and covered with water and then the sealable lid 118 is placed on the container 120. According to some embodiments, upon actuation of a user input device (described in more detail below), the microprocessor 142 closes the relay 144 to start the vacuum pump 112. The microprocessor 142 monitors the air pressure from the air pressure gauge 132 and controls the air pressure by turning the valve 134 using the stepper motor 148. When the correct air pressure is reached, the microprocessor 142 closes the relay 146 to start the shaker 124 and begin the shaking process. During the shaking process the microprocessor 142 monitors the vacuum air pressure and adjusts the valve 134 to maintain the correct air pressure. In addition, the microprocessor 142 may monitor and store data from the accelerometer 154. When the microprocessor 142 measures 15 minutes of shaking time, the shaker 124 is stopped by opening the shaker relay 146. The pump 112 is stopped by opening the vacuum pump relay 144 and the valve 134 is opened to allow the container 120 to come to equilibrium with atmosphere.

Figure 3:
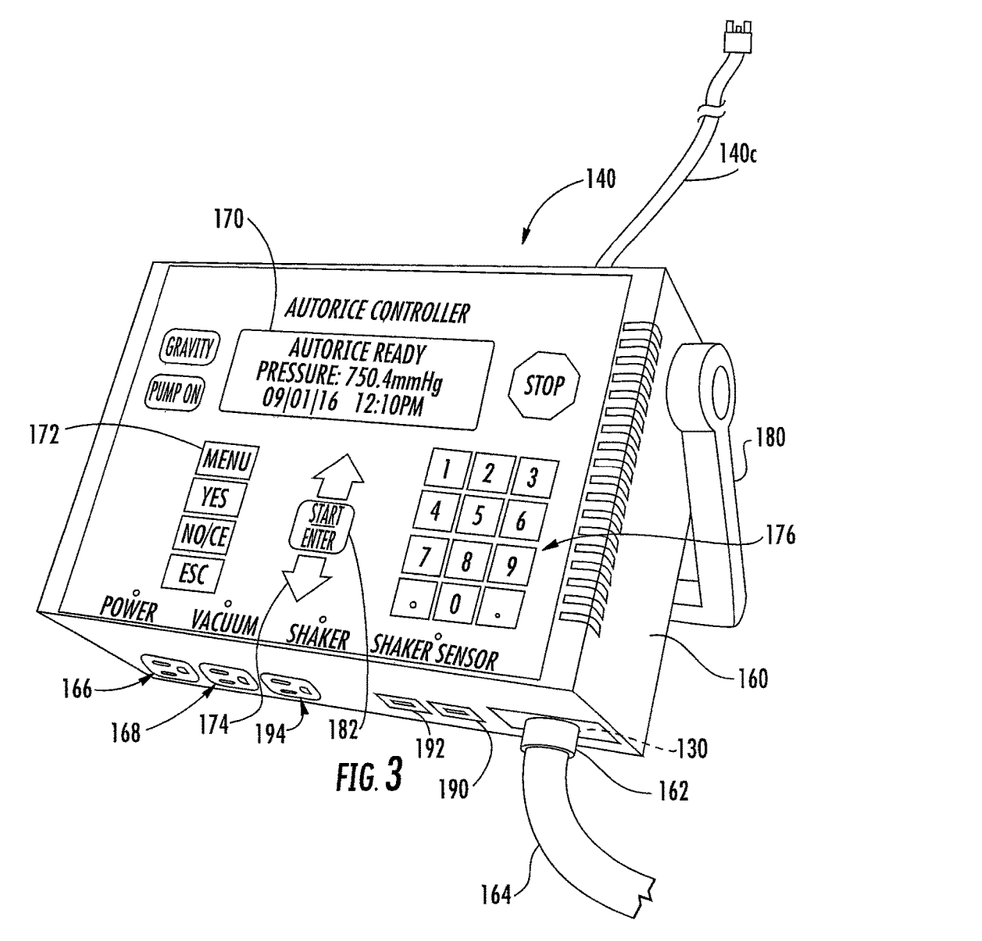
FIG. 3 is a perspective view of an exemplary controller of the system of FIG. 2 according to some embodiments of the invention.

The controller or control unit 140 according to some embodiments is illustrated in FIG. 3. The controller 140 includes a housing 160. The various components shown in the dashed box of FIG. 2 may be in or on the controller housing 160. It will be understood that the various components in the dashed box of FIG. 2 or the housing 160 of FIG. 3 are electrically connected to one another. According to some embodiments, the junction 130 is also in or on the housing 160. An inlet port connection 162 (which may correspond to or be connected to the junction 130) is on the housing 160 and is configured to connect to or receive a hose or tubing 164 that is connectable to the junction 116 (FIG. 2). The port connection 162 is in fluid communication with the pressure gauge 132 and the valve 134 (FIG. 2) in the housing 160.

A vacuum pump electrical outlet 166 on the housing 160 is configured to receive a power connection or cord 112c (FIG. 2) of the vacuum pump 112. A shaker electrical outlet 168 is also on the housing 160 and is configured to receive a power connection or cord 124c of the shaker 124. The controller 140 may be connected to power using a plug-in power cord 140c to thereby provide power to the vacuum pump 112 and the shaker 124.

As described above, the cord 154c may be used to connect the accelerometer 154 to the controller 140. The controller 140 may include a port 192 configured to receive the cord 154c so that the accelerometer and the controller 140 are in communication. For example, the port 192 may be a USB port and the cord 154c may be a USB cord, although those skilled in the art will recognize that other configurations are possible.

A display 170 can be provided on the housing 160. The display 170 may display operational parameters during the test such as date and time, vacuum pressure in the container 120, time elapsed or remaining for the test, and so forth. Also, the housing can include a user input device illustrated as a plurality of buttons. It will be understood that the user input device can be implemented in other ways; for example, the user input device could be included in a touch sensitive display (which may be included with the display 170 or may be a different display).

A user may press the menu button 172 such that menu options are displayed on the display 170. A user may use the up and down arrow buttons 174 to scroll through the menu options and may use numeric keypad buttons 176 to set values associated with the menu options. For example, a user may set the shaking time, the vacuum dwell time (the time that the vacuum is held before the shaker starts), the target vacuum and/or the vacuum offset. The vacuum offset may be used to adjust the target vacuum to match a vacuum reading in the container 120. The length of hose between the vacuum pump 112 and the pressure sensor or vacuum gauge 132 in the controller 140 (e.g., 116a and 116b) may cause a pressure drop with a resulting difference between the reading of the vacuum gauge 132 and the actual vacuum in the container 120. For example, if a vacuum gauge 178 at the container 120 has a reading of 29.5 mmHg and the controller 140 has a reading of 27.5 mmHg, the user may enter a −2 mmHg offset to account for the pressure drop in the hose. Alternatively, all or some of these settings can be default and/or automatically generated and selected.

The controller 140 may be lightweight and/or portable. The controller 140 may be less than 10 pounds and, according to some embodiments, is about five pounds. The controller 140 may be dimensioned to have an external volume of less than 450 cubic inches. The controller 140 may be configured to fit on a benchtop or mount to a wall. For example, the controller 140 may include a rotatable arm stand 180 coupled to the housing 160.

Figure 4:
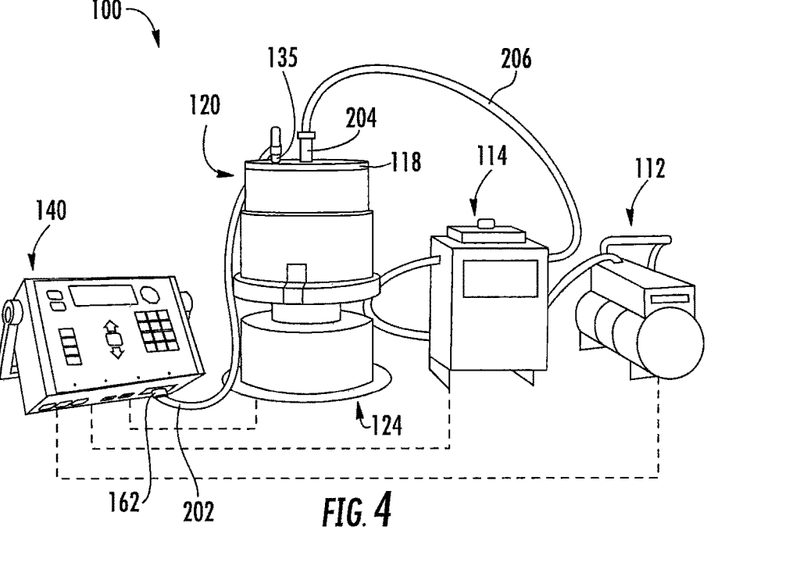
FIG. 4 is a perspective view of the system of FIG. 2 according to some embodiments.

FIG. 4 illustrates the system 100 more generally. The dashed lines in FIG. 4 indicate that the controller 140 is configured to operate and/or control the vacuum pump 112, the dryer 114 and/or the shaker 124. The dryer 114 may be an electrical cold trap or moisture trap. In this case, a power cord plug or connection of the moisture trap may be received in an electrical outlet 194 on the controller 140 (FIG. 3) to provide power to the moisture trap 114.

As described above, the junction 116 illustrated in FIG. 2 may be omitted. As illustrated in FIG. 4, a hose or tubing 202 may extend from the inlet port 162 of the controller 140 to the inlet port 135 of the lid 118 or the container 120 to thereby place the controller 140 (as well as the vacuum gauge 132 and the valve 134 shown in FIG. 2) and the container 120 in fluid communication with one another. The lid 118 or the container 120 may also include a vacuum port 204. A hose or tubing 206 may place the container 120 and the vacuum pump 112 in fluid communication with one another (e.g., via the moisture trap 114). This configuration can provide the same functionality and advantages described herein.

Figure 5:
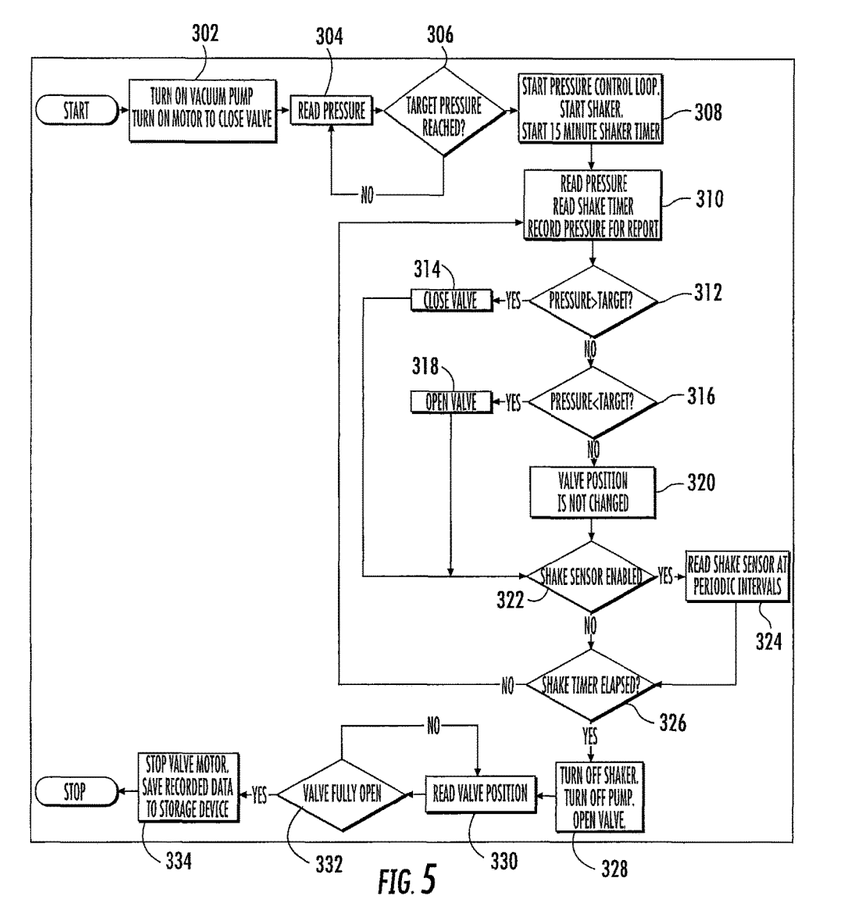
FIG. 5 is a flowchart illustrating operations according to some embodiments of the invention.

FIG. 5 is a flowchart illustrating operations according to embodiments of the invention. With reference to FIGS. 2-4, the controller 140 turns on the vacuum pump 112 and/or turns on the motor 148 to close the valve 134 (Block 302), for example responsive to an operator pressing a start button 182 on the controller 140. The air pressure sensor 132 senses the air pressure in the container 120 and communicates the signal to the controller 140 (Block 304). The air pressure sensor 132 continues to sense the air pressure (e.g., continuously or repeatedly) and communicate the signal to the controller 140 which determines whether the target pressure has been reached (Decision 306).

Once the target pressure has been reached, the controller 140 starts a pressure control loop, starts the shaker 124 and/or starts a 15 minute timer for the shaker 124 (Block 308). At Block 310, the controller reads the pressure in the container 120, reads the time for the shaker 124 and/or records the pressure in the container for a report (Block 310). At Decision 312, the controller 140 determines whether the pressure in the container 120 is greater than the target pressure and, if so, commands the motor 148 to close the valve 134 (Block 314). At Decision 316, the controller 140 determines whether the pressure in the container 120 is less than the target pressure and, if so, commands the motor 148 to open the valve 134 (Block 318). If the pressure in the container 120 is within a predetermined range of the target pressure (e.g., 27.5±2.5 mmHg), the valve position is not changed (Block 320).

The controller 140 may determine whether the shaker sensor or accelerometer 154 is active (Decision 322). If the shaker sensor is active, the controller 140 receives a signal from the accelerometer 154 at periodic intervals (Block 324).

The controller 140 determines whether the shaker timer time has reached 15 minutes (Decision 326). If not, the operations beginning at Block 310 are repeated. If the shaker timer has reached 15 minutes, the controller 140 turns off the shaker 124, turns off the vacuum pump 112 and/or opens the valve 134 (Block 328). The controller 140 determines the position of the valve 134 (e.g., using the encoder 150) (Block 330). If the controller 140 determines that the valve 134 is fully open (Decision 332) then the controller 140 stops the valve motor 148 and/or saves recorded data from the test (Block 334). For example, the controller 140 may save the data to internal memory and/or an external storage device. The controller 140 may also transmit the data to a server or cloud and/or transmit the data to a user device (e.g., wirelessly to a smart phone or other computer device).

As described above, in the conventional manual system, the technician monitors the pressure in the container and turns a valve in an effort to maintain the vacuum pressure at 27.5 mmHg. In the system illustrated in FIGS. 2 and 3, the controller 140 automatically monitors the pressure read by the pressure sensor 132 and automatically determines if the valve 134 should be moved or turned. The controller 140 may automatically monitor the pressure reading multiple times per second. If the pressure is too high, too much air is entering the system and the valve 134 is automatically turned in one direction so that less air enters the system. If the pressure is too low, too little air is entering the system and the valve 134 is automatically turned in the opposite direction to let more air in the system.

According to some embodiments, the controller 140 determines which direction to turn the valve 134 and/or the speed to turn the valve 134. The software may generate an error signal that is proportional to the difference between the desired (target) pressure and the actual pressure. If the pressure is too high, a negative error signal may be generated, and the valve is closed. If the pressure is too low, a positive error signal may be generated, and the valve is opened.

As described above, the stepper motor 148 may be used to turn the valve 134, although other motors such as rotary motors may be used. The controller 140 may command the motor (or a controller thereof) to move at a speed that is proportional to the error in the pressure reading. The controller 140 continues to monitor the pressure and commands the motor to stop turning when the pressure is within the proper limits or the error in pressure is zero.

The controller 140 uses a motor position indicator to determine when the motor has reached its fully opened and closed positions. As described above, the motor position indicator may be the rotary shaft encoder 150, although other devices such as a micro-switch, a proximity sensor or the like may be used. The encoder 150 is connected to the motor shaft and generates a signal when the shaft turns. This signal is read by the controller 140. When the velocity of the motor as indicated by the encoder 150 is less than the velocity that the controller 140 is commanding the motor to turn, the motor is considered stalled, and this indicates the limits of its travel. In response, the controller 140 stops the command to rotate the motor. This helps prevent the motor from over-tightening and jamming the fine threaded valve (e.g., the valve 134).

As described above, the Rice test standard states that the shaking of the sample must take place for 15 minutes after the proper pressure is reached. According to some embodiments, the system uses two AC relays that control two AC outlets. Referring to FIGS. 2 and 3, the outlet 166 is for the vacuum pump 112 and the outlet 168 is for the shaker 124. The controller 140 starts the process by turning on the vacuum pump 112 through the vacuum pump relay 144 and controls the valve 134 until a target pressure (e.g., 27.5 mmHg) is reached. The shaker 124 is then turned on through the shaker relay 146. The controller 140 monitors the elapsed time and pressure for a predetermined amount of time (e.g., 15 minutes). The vacuum pressure is adjusted to stay within a predefined range (e.g., 27.5±2.5 mmHg) and at the end of the predetermined amount of time the vacuum pump 112 and the shaker 124 are turned off by opening the relays 144, 146. The controller 140 then opens the valve 134 to let air into the container 120.

To help ensure that the pressure remains within the proper limits, the pressure data may be recorded during the test (e.g., every 15 seconds). The data is then available for a user to view after the test. Referring to FIG. 3, the controller 140 may include a storage device port such as a USB port 190 to receive a USB data storage device with the controller 140 configured to transfer the data to the storage device. It is contemplated that the data could be sent to the user in other ways. For example, the controller 140 may include an RS232 port, a Bluetooth module including transmitter or transceiver, a Wi-Fi module including a transmitter or transceiver or similar wireless technology that could be used to wirelessly send the data to a computer, tablet, smart phone or other handheld device. It is also contemplated that the controller 140 may wirelessly send messages to a user or lab device to indicate the progress of the Rice test.

The accelerometer 154 (FIG. 2) may be a three-axis accelerometer. The accelerometer 154 is used to measure the shaking force and shaking frequency applied to the sample. The accelerometer data may be sampled many hundreds of times per second during the shaking process. The data may then be processed using frequency analysis providing the acceleration in each axis in $m/s^2$ or in g's (9.8 $m/s^2$). This information can be recorded and delivered to the user in the same or similar way as described above in reference to the pressure data.

A figure of merit may be determined to provide the user information on how much force is applied during the shaking. According to some embodiments, this figure of merit is called the shaker factor or S-factor.

The first step in calculating the S-factor is determining the frequency of shaking that has the peak acceleration (e.g., using the controller 140). This can be performed using a signal processing tool such as Fast Fourier Transform (FFT), Discrete Fourier Transform (DFT) or the Goertzel algorithm. The controller 140 then determines the frequency that has the maximum value (peak frequency value). This frequency is found to be the same in each axis using a typical shaker used in the industry. Next, Parseval's theorem (the total energy contained in a waveform x(t) summed across all of the time t is equal to the total energy of the waveform's Fourier transform X(f) summed across all of its frequency components f) is used to find the total acceleration force in the system. The acceleration force is determined in each axis, and then the vector result is determined and converted to $m/s^2$. The final S-factor is this force times the frequency which provides a term in $m/s^3$.

The accelerometer 154 can be placed on the container lid 118, the container 120 or the shaker 124. The S-factor may be different when the accelerometer is placed in different positions. The value measured in a particular location can be used to monitor shaking quality from test to test. The proper S-factor and frequency can be determined by the user. Users can vary the shaking frequency on their shaker units for mixtures in their area and determine the proper settings to help ensure that samples are not compacting, trapping air or stripping.

The shaking acceleration, frequency and/or shaker factor may be displayed on the controller display 170. Additionally or alternatively, the shaking acceleration, frequency and/or shaker factor may be provided in a report (which may also include the test data such as date and time and/or vacuum pressure in the container).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A system for a maximum specific gravity test, the system comprising:
   a sealable container sized and configured to receive and hold an asphalt mixture sample;
   a vacuum pump in fluid communication with the container and configured to evacuate the container;
   a valve in fluid communication with the container and configured to adjust vacuum pressure in the container;
   a shaker with the container on the shaker, the shaker configured to shake the container; and
   a controller configured to operate the system in a test mode by: (i) turning on the vacuum pump; then (ii) automatically monitoring a vacuum pressure in the container with the vacuum pump on; then (iii) automatically turning on the shaker when the monitored vacuum pressure reaches a target vacuum pressure value; then (iv) automatically opening or closing the valve such that the monitored vacuum pressure in the container is maintained within a target vacuum pressure range for a predetermined period of time with the shaker on; and then (v) automatically turning the shaker off at the end of the predetermined period of time;
   wherein the target vacuum pressure value is 27.5 mmHg and/or wherein the target vacuum pressure range is 27.5±2.5 mmHg.

2. The system of claim 1 wherein the target vacuum pressure value is 27.5 mmHg.

3. The system of claim 1 wherein the target vacuum pressure range is 27.5±2.5 mmHg.

4. The system of claim 1 wherein the predetermined period of time is 15 minutes.

5. The system of claim 1 wherein the controller comprises a housing with a vacuum power outlet on the housing for receiving a power connection from the vacuum and a shaker power outlet on the housing for receiving a power connection from the shaker.

6. The system of claim 5 wherein the valve is in the controller housing.

7. The system of claim 6 further comprising:
a vacuum port configured to receive tubing that is in fluid communication with the container;
a pressure gauge in the controller housing and in fluid communication with the vacuum port, the pressure gauge configured to detect the vacuum pressure in the container; and
a motor in the controller housing and operatively associated with the valve, wherein the controller is configured to operate the motor for opening or closing the valve responsive to signals received from the pressure gauge indicating the vacuum pressure in the container.

8. The system of claim 5 wherein the controller comprises a user input device on the housing, and wherein the controller is configured to turn the vacuum pump on responsive to actuation of the user input device.

9. The system of claim 5 wherein the controller comprises a display on the housing, the display configured to display operational parameters including the monitored vacuum pressure in the container.

10. The system of claim 1 wherein the controller is configured to generate and save a data file including the date and time and/or the monitored vacuum pressure every 5 to 60 seconds for respective test samples when the system is operating in the test mode.

11. A system for a maximum specific gravity test, the system comprising:
a sealable container sized and configured to receive and hold an asphalt mixture sample;
a vacuum pump in fluid communication with the container and configured to evacuate the container;
a valve in fluid communication with the container and configured to adjust vacuum pressure in the container;
a shaker with the container on the shaker, the shaker configured to shake the container;
a controller configured to operate the system in a test mode by: (i) turning on the vacuum pump; then (ii) automatically monitoring a vacuum pressure in the container with the vacuum pump on; then (iii) automatically turning on the shaker when the monitored vacuum pressure reaches a target vacuum pressure value; then (iv) automatically opening or closing the valve such that the monitored vacuum pressure in the container is maintained within a target vacuum pressure range for a predetermined period of time with the shaker on; and then (v) automatically turning the shaker off at the end of the predetermined period of time; and
an accelerometer in communication with the container and the controller, wherein the controller is configured to display and/or save acceleration and/or frequency of shaking based on signals received from the accelerometer when the system is operating in the test mode.

12. The system of claim 11 wherein the controller is configured determine a shaker factor by multiplying the acceleration and the frequency of shaking, and wherein the controller is configured to display the shaker factor and/or generate and save a data file including the shaker factor.

13. A method for a maximum specific gravity test, the method comprising:
placing an asphalt mixture sample in an interior of a container that is held on a shaker;
adding liquid to the interior of the container to submerge the asphalt mixture sample;
sealing the interior of the container using a lid;
automatically turning on a vacuum pump that is in fluid communication with the interior of the container to evacuate the interior of the container;
automatically monitoring a vacuum pressure in the interior of the container using a controller;
automatically turning on the shaker when the monitored vacuum pressure is about 27.5 mmHg using the controller;
using the controller, automatically opening a valve that is in fluid communication with the container if the monitored vacuum pressure falls below 27.5 mmHg by a first prescribed amount;
using the controller, automatically closing the valve if the monitored vacuum pressure exceeds 27.5 mmHg by a second prescribed amount; and
automatically turning off the shaker about 15 minutes after automatically turning on the shaker.

14. The method of claim 13 further comprising using an accelerometer in communication with the container to determine an acceleration and a frequency that the shaker is shaking the asphalt mixture sample after automatically turning on the shaker.

15. A control unit for automating a maximum specific gravity test, the control unit comprising:
a housing;
a vacuum pump outlet on the housing for electrically connecting a vacuum pump to the control unit;
a shaker outlet on the housing for electrically connecting a shaker to the control unit;
an inlet port on the housing for fluidly connecting a container to the control unit, the container being on the shaker and in fluid communication with the vacuum pump;
a valve in the housing and in fluid communication with the inlet port;
wherein the control unit is configured to turn on the vacuum pump, to automatically monitor a vacuum pressure in the container with the vacuum pump on, to automatically turn on the shaker when the monitored vacuum pressure reaches about 27.5 mmHg, to automatically open or close the valve when the monitored vacuum pressure falls outside the range of 27.5 mmHg±2.5 mmHg, and to automatically turn off the shaker 15 minutes after automatically turning on the shaker.

16. The control unit of claim 15 further comprising:
a pressure gauge in the housing and in fluid communication with the inlet port; and
a motor operatively coupled to the valve;
wherein the controller is configured to automatically monitor the vacuum pressure in the container using the pressure gauge and the automatically open and close the valve using the motor.

17. The control unit of claim 15 wherein the control unit is configured to generate a report of a respective asphalt mix sample including the monitored vacuum pressure over time.

18. The control unit of claim 17 wherein the control unit is configured to save the report as a data file, the control unit further comprising (i) a data storage device port configured to receive a data storage device for loading the report on the memory device and/or (ii) a wireless module for wirelessly transmitting the report to a user device.

19. The control unit of claim 15 further comprising a moisture trap outlet on the housing for electrically connecting a moisture trap to the control unit.

20. The system of claim 11 wherein the target vacuum pressure range is 27.5±2.5 mmHg and/or the predetermined period of time is 15 minutes.

* * * * *